United States Patent [19]

Schwartz et al.

[11] Patent Number: 6,013,495
[45] Date of Patent: Jan. 11, 2000

[54] METHODS OF USE FOR INTEGRIN $B_{1C}$ CELL GROWTH INHIBITOR

[75] Inventors: Martin A. Schwartz, Poway; Jere E. Meredith, Jr.; Yoshikazu Takada, both of San Diego, all of Calif.; Lucia Languino, Milford, Conn.

[73] Assignee: The Scripps Research Institute, La Jolla, Calif.

[21] Appl. No.: 08/951,200

[22] Filed: Oct. 14, 1997

Related U.S. Application Data

[62] Division of application No. 08/327,118, Oct. 21, 1994, abandoned.

[51] Int. Cl.[7] ............................. C12N 1/38; C12N 13/00; C07K 7/08; C07K 14/435
[52] U.S. Cl. ....................... 435/173.1; 435/375; 530/324; 530/327; 514/12; 514/14
[58] Field of Search ................................. 435/375, 173.1; 514/12, 14; 530/324, 327

[56] References Cited

U.S. PATENT DOCUMENTS 5,498,694  3/1996  Ruoshahti .
5,536,814  7/1996  Ruoslahti ................................. 530/329

OTHER PUBLICATIONS

Pasqualini, R and Hemler, ME. J. Cell Biol. 125(2):447–460, Apr. 1994.
Teague, T.K., and McIntyre, B.W. Cell Adhes. Comm. 2:169–184, 1994.
Fenczik, C.A. Nature. 390:81–85, Nov. 6, 1997.
Languino et al. (1992) J. Biol. Chem. 267, 7116–7120.
LaFlamme et al. (1992) J. Cell. Biol. 117, 437–447.
Ruoshati et al. (1994) Cell, 77, 477–478.

*Primary Examiner*—Christina Y. Chan
*Assistant Examiner*—Mary Beth Tung
*Attorney, Agent, or Firm*—Fish & Richardson P.C.

[57] ABSTRACT

The present invention provides a method for inhibiting cell proliferation in a cell comprising contacting the cell with a nucleic acid sequence or a polypeptide having essentially the sequence of the $\beta_{1C}$ integrin. Also included in the invention are peptides consisting of amino acid residues which are the size of or fewer than the sequence of the cytoplasmic domain of the $\beta_{1C}$ integrin consisting essentially of the amino acid sequence of SEQ ID NO:1 and SEQ ID NO:2, and functional fragments thereof which are useful for inhibiting cellular proliferation. Peptides, polynucleotides, and antibodies immunoreactive with the peptides, and methods of use for inhibiting cell growth are also provided.

4 Claims, 6 Drawing Sheets

C-TERMINAL DOMAIN OF $\beta_1$ AND $\beta_{1C}$ INTEGRINS $\beta_1$    AKWDT $_{778/2435}$GENPIYKSAVTTVVNPKYEGK$_{798/2498}$ $\beta_{1C}$    AKWDT $_{778/2435}$SLSVAQPGVQWCDISSLQPLTS-
RFQQFSCLSLPSTWDYRVKILFIRVP$_{825/2578}$

*FIGURE 1A*

β₁ INTEGRIN

```
2420  GCC AAA TGG GAC ACG* GGT GAA AAT CCT ATT TAT
773    A   K   W   D   T    G   E   N   P   I   Y

2453  AAG AGT GCC GTA ACA ACT GTG GTC AAT CGG AAG
784    K   S   A   V   T   T   V   V   N   R   K

2486  TAT GAG GGA AAA
795    Y   E   G   K
```

*FIGURE 1B-1*

β₁C INTEGRIN

```
2420  GCC AAA TGG GAC ACG* TCT CTC TCT GTC GCC CAG
773    A   K   W   D   T    S   L   S   V   A   Q

2453  CCT GGA GTG CAG TGG TGT CAT ATC AGC TTA CTG
784    P   G   V   Q   W   C   D   I   S   L

2486  CAA CCT CTG ACT TCC AGA TTC CAG CAA TTC TCC
795    Q   P   L   T   S   R   F   Q   Q   F   S

2519  TGC CTC AGC CTC CCG AGT ACC TGG GAT TAC AGG
806    C   L   S   L   P   S   T   W   D   Y   R

2552  GTG AAA ATC CTA TTT ATA AGA GTG CCG
817    V   K   I   L   F   I   R   V   P

2579  CAACAACTCTGGTCAATCCGAAGTATGAGGGAAAA
```

*FIGURE 1B-2* poly-linker: XhoI-XbaI-SfiI-NotI-RI-RV-H3-ClaI-(SalI/XhoI)
             1         1         1  2

METHODS OF USE FOR INTEGRIN $B_{1C}$ CELL GROWTH INHIBITOR

This invention is a divisional of U.S. application Ser. No. 08/327,118 filed Oct. 21, 1994, now abandoned.

This invention was made with government support under Contract Nos. HL 07695, GM 47214, and HL 48728 awarded by the National Institutes of Health. The government has certain rights in this invention.

BACKGROUND OF THE INVENTION

1. Field of the Invention

This invention relates generally to the field of cell-surface glycoproteins and specifically to the use of integrin $B_{1C}$ and cytoplasmic peptides thereof, for inhibition of cell growth.

2. Description of Related Art

Integrins are a family of cell surface glycoproteins which mediate cell-cell and cell-extracellular matrix interactions and play an important role in processes such as cell migration, tissue repair and tumor invasion (Hynes, R., *Cell* 48:549, 1987; Ruoslahti and Giancotti, *Cancer Cells* 1:119, 989). They are heterodimers composed of non-covalently linked α and β subunits which associate in different combinations generating several receptor complexes with distinct binding specificities.

The β1 class of integrins is found in various combinations to form integrins with different functions. For example, the α1/β1 and the α2/β1 are receptors for collagens; the α3/β1 has broad specificity and binds to collagen, fibronectin and laminin; the α4/β1 is a receptor that mediates lymphocytes-target adhesion during cytolysis as well as the interaction of lymphocytes with endothelial cells; the α5/β1 and the α6/β1 complexes are receptors specific for fibronectin and laminin, respectively. Both α and β subunits are transmembrane proteins that provide a linkage between the extracellular matrix protein and actin, and are located in specialized areas of the plasma membrane called focal contacts (Damsky, et al., *J. Cell Biol.,* 100:1528, 1985).

The cytoplasmic domains of the integrins play an important role in integrin functions. First, recent studies have shown that the cytoplasmic domain of the β2 subunit modulates the affinity of the αLβ3 integrin (LFA-1) for its ligand, ICAM-1 (Hibbs, et al., *Science,* 251:1611, 1991). Second, tyrosine phosphorylation of the β1 subunit cytoplasmic domain has been found to reduce the binding of the fibronectin receptor to fibronectin extracellularly and to talin inside the cell (Tapley, et al., *Oncogene* 4:325, 1989). Third, truncation of the β1 subunit cytoplasmic domain can abolish the ability of the β1 integrins to localize in adhesion plaques (Marcantonio, et al., *Cell Reg.,* 1:597, 1990).

Recently, several cytoplasmic terminal variants for the human β1 integrin ($β_{1A}$) (Argraves, et al., *J. Cell Biol.,* 105:1183, 1987) have been identified. One such variant, $β_{1B}$ described by Altruda, et al., (Gene, 95:261, 1990), is 9 amino acids shorter than the corresponding domain of β1 and contains unique C-terminal sequences. A second variant, $β_{1C}$, was identified as an alternative splice variant of β1 that contains an insert of 116 nucleotides which produces a frame shift in the native β1 nucleotide sequence and codes for a unique 48-amino acid C-terminus (Languino and Ruoslahti, *J. Biol. Chem.,* 267:7116, 1992).

Although various β1 integrin variants have been identified, the function for these polypeptides has been unclear. The present invention provides a biological activity for the $β_{1C}$ variant, including methods of use for the full length polypeptide as well as functional cytoplasmic fragments of the polypeptide.

SUMMARY OF THE INVENTION

The present invention is based on the seminal discovery of the biological activity of $β_{1C}$ integrin as a cell growth inhibitor. $β_{1C}$ is an alternative splice variant of the $β_1$ integrin and differs from $β_1$ by including a unique cytoplasmic region. In contrast to native $β_1$, the cytoplasmic domain of $β_{1C}$ imparts a cell proliferative inhibitor activity on the polypeptide.

Thus, in one embodiment, the invention provides a method for treating a cellular proliferative disorder in a subject, comprising administering to the subject with the disorder a therapeutically effective amount of $β_{1C}$ integrin reagent which inhibits cellular proliferation. A $β_{1C}$ integrin reagent includes polynucleotide or polypeptide sequences encoding $β_{1C}$ integrin and cytoplasmic fragments thereof. In addition, a $β_{1C}$ reagent as used herein includes anti-idiotype antibodies which bind to a paratope of an antibody which binds to the amino acid sequence of the peptide of SEQ ID NO:1.

In another embodiment, the invention provides a method of inhibiting cell proliferation in a cell comprising contacting the cell with a nucleic acid having essentially the nucleic acid sequence encoding integrin $β_{1C}$, SEQ ID NO:1 or SEQ ID NO:2, or functional fragments thereof and a method of inhibiting cell proliferation in a cell comprising contacting the cell with a polypeptide having essentially the amino acid sequence of integrin $β_{1C}$, SEQ ID NO:1 or SEQ ID NO:2, or functional fragments thereof.

The invention also includes isolated peptides consisting essentially of the unique 48 amino acids of $β_{1C}$ (SEQ ID NO:1) and the last 14 C-terminal amino acids of $β_{1C}$ (SEQ ID NO:2), and polynucleotide sequences encoding the peptides.

BRIEF DESCRIPTION OF THE DRAWINGS

FIG. 1A shows a comparison of the amino acid sequence of the C-termini of $β_1$ (SEQ ID NO:6)(SEQ ID NO:1) and $β_{1C}$ integrins. (numbers shown indicate the amino acid number/nucleotide numbers). Sequences are shown $NH_2$ to COOH and 5' to 3'.

FIG. 1B shows a comparison of the nucleotide and amino acid sequence of the C-terminii of $β_1$ and $β_{1C}$ integrins. The asterisk indicates the alternatively spliced exon. The 116-bp insert in $β_{1C}$ produces a frame shift in the 3' end of the $β_1$ sequence. Sequences are shown $NH_2$ to COOH and 5' to 3'.

DETAILED DESCRIPTION OF THE INVENTION

Figure 2:
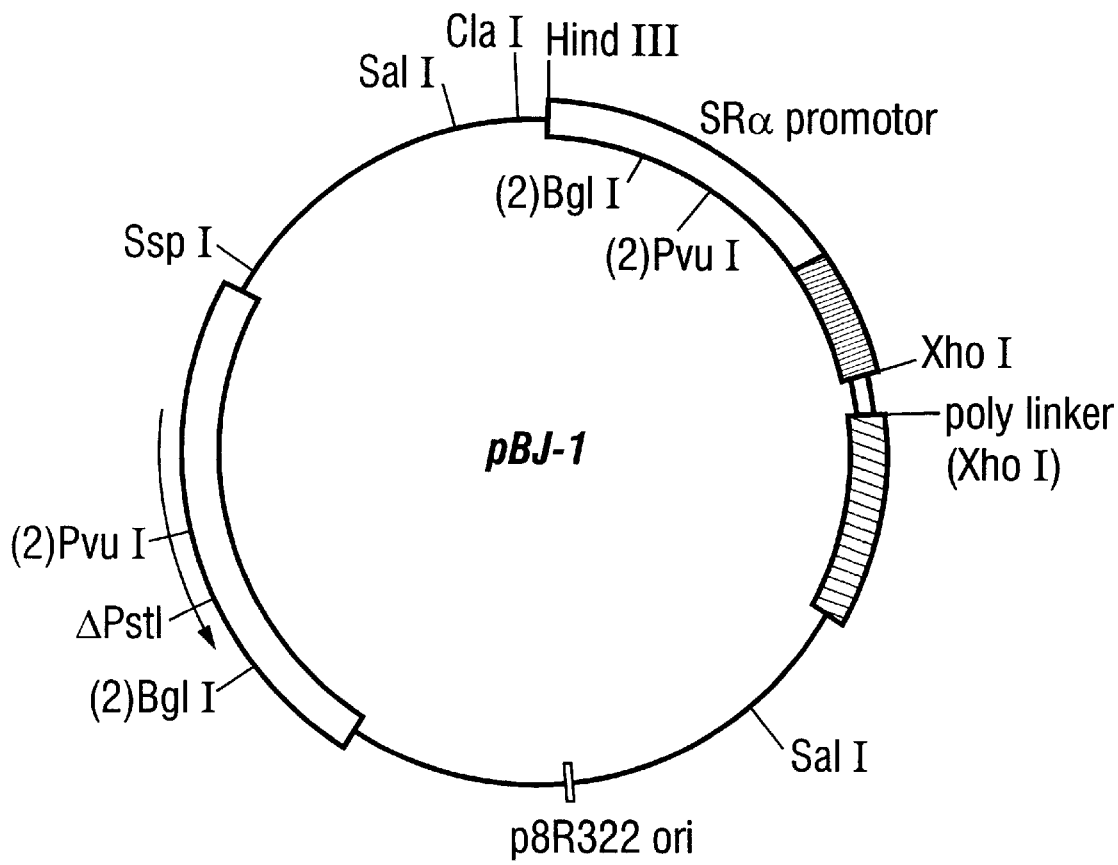
FIG. 2 shows a vector map for pBJ-1 plasmid vector.

The present invention provides a method of use for the alternative splice variant of integrin $\beta_1$ subunit, $\beta_{1C}$. For the first time, the present invention shows that this splice variant, which contains 48 unique amino acids in the cytoplasmic domain of the wild type $\beta_1$ integrin, is involved in the regulation of proliferation in a cell, and specifically, the $\beta_{1C}$ polypeptide inhibits DNA synthesis. Based on this discovery, synthetic peptides from the unique cytoplasmic region of the polypeptide can be used to inhibit DNA synthesis in a cell. The discovery of the functional properties of the $\beta_{1C}$ integrin has led to the development of novel methods and compositions for inhibiting cellular proliferation.

As used herein, the term "synthetic peptide" denotes a peptide which does not comprise an entire naturally occurring protein molecule. These peptides are "synthetic" in that they may be produced by human intervention using such techniques as chemical synthesis, recombinant genetic techniques, or fragmentation of whole receptor or the like.

The peptides of the invention range in length from about 10 to about 100 amino acids and include amino acid sequences which correspond to amino acid residues 778–825 of the $\beta_{1C}$ subunit, or SLSVAQPGVQWCDISS-LQPLTSRFQQFSCLSLPSTWDYRVKILFIRVP (SEQ ID NO:1) or amino acids 812–825 of the $\beta_{1C}$ subunit, or TWDYRVKILFIRVP (SEQ ID NO:2). These sequences represent surface oriented peptides of the cytoplasmic domain of the $\beta_{1C}$ subunit. Therefore, the peptide of SEQ ID NO:1 contains a critical domain (SEQ ID NO:2) for the inhibition of DNA synthesis and cell proliferation. A deletion mutant of $\beta_{1C}$ integrin polypeptide lacking SEQ ID NO:2, is unable to inhibit DNA synthesis in a cell.

The peptides of the invention include "functional fragments" from the cytoplasmic domain of $\beta_{1C}$ subunit, as long as the DNA synthesis inhibitory activity of the peptide, as noted above, remains. Smaller peptides containing the biological activity of SEQ ID NO:1 are included in the invention. For example, SEQ ID NO:2 is one such peptide. Other peptides can be readily identified by those of skill using the routine screening methods described herein without resorting to undue experimentation. For example, the peptides can be assayed by standard DNA synthesis assays, such as labeled 5-bromodeoxyuridine (BdrU) incorporation or incorporation of radiolabeled tritiated thymidine to determine whether the peptide of interest contains the DNA synthesis inhibition activity of $\beta_{1C}$. Other DNA synthesis assays will be known to those of skill in the art. These peptides can be as few as 5, preferably as few as 10 amino acids in length.

Minor modifications of the primary amino acid sequence of the $\beta_{1C}$ polypeptide or peptides of the invention may result in peptides which have substantially equivalent activity as compared to the specific peptides described herein. Such modifications may be deliberate, as by site-directed mutagenesis, or may be spontaneous. All of the peptides produced by these modifications are included herein as long as the biological activity of the original peptide still exists.

Further, deletion of one or more amino acids can also result in a modification of the structure of the resultant molecule without significantly altering its biological activity. This can lead to the development of a smaller active molecule which would also have utility. For example, one of skill in the art can use standard techniques to remove amino or carboxy terminal amino acids from SEQ ID NO:1, as embodied by SEQ ID NO:2, as long as the amino acids are not required for biological activity of the particular peptide. Therefore, as demonstrated by SEQ ID NO:2, the last 14 amino acids of the peptide of SEQ ID NO:1 may still act as an inhibitor of DNA synthesis.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "coservative variation " also includes the use of a substituted amino acid in place of an unsubstituted parent amino acid provided that antibodies raised to the substituted polypeptide also immunoreact with the unsubstituted polypeptide. Peptides which contain a biological activity of a peptide of the invention can be easily identified using standard assays, such as the BdrU DNA synthesis assay exemplified herein.

Peptides of the invention can be synthesized by such commonly used methods as t-BOC or FMOC protection of alpha-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Peptides of the invention can also be synthesized by the well known solid phase peptide synthesis methods described by Merrifield, (*J. Am. Chem. Soc.*, 85:2149, 1962), and Stewart and Young, (*Solid Phase Peptides Synthesis*, Freeman, San Francisco, 1969, pp. 27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The peptides of the invention can be used singularly, in mixtures, or as multimers such as aggregates, polymers, and the like. Thus, the invention embraces synthetic peptides which comprise one or more of the same, or different, peptides of the invention to produce a homogeneous or heterogeneous polymer with respect to the particular peptides of the invention which are contained therein. Appropriate techniques for producing various mixtures, aggregates, multimers and the like will be known to those of skill in the art. For example, the invention would include a peptide comprising SEQ ID NO:1 and SEQ ID NO:2 or other DNA synthesis inhibitory peptides, wherein SEQ ID NO:1, SEQ ID NO:2 and/or other peptides are linked directly or indirectly, for example, by using a spacer or linker moiety. Such moieties and their use are well known to those of skill in the art.

The invention also provides isolated nucleic acid sequences or polynucleotides which encode the $\beta_{1C}$ polypeptide or $\beta_{1C}$ cytoplasmic peptides of the invention. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code.

The polynucleotide encoding the peptides of the invention includes a polynucleotide that encodes SEQ ID NO:1, or full length $\beta_{1C}$, as well as complementary nucleic acid sequences. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the peptides of the invention under physiological conditions.

Polynucleotide sequences encoding the peptides of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

The development of specific DNA sequences encoding the peptides of the invention can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. In addition, the peptides of the invention can be obtained by polymerase chain reaction (PCR).

Of the above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for $\beta_{1C}$ peptides having at least one epitope, using antibodies specific for this region. Such antibodies can be either polyclonally or monoclonally derived and used to detect expression product indicative of the presence of $\beta_{1C}$ cDNA.

DNA sequences encoding the peptides of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the $\beta_{1C}$ peptide nucleotide sequences may be inserted into a recombinant expression vector. The term "recombinant expression vector" refers to a plasmid, virus or other vehicle known in the art that has been manipulated by insertion or incorporation of the $\beta_{1C}$ peptide genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters). Promoter sequences include both inducible and constituitive promoters, as well as tissue specific promoters. Such promoters will be known to those of skill in the art and are used depending on the tissue or cell type desired to be contacted.

Polynucleotide sequences encoding $\beta_{1C}$ polypeptide or peptides of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the peptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies. In addition, the use of a carrier/fusion protein system, such as glutathione-S-transferase (GST) or other carriers known in the art, can be used to purify recombinantly produced proteins of the invention.

In another embodiment, the invention provides a method for inhibiting cell proliferation in a cell comprising contacting the cell with a nucleic acid having essentially the nucleic acid sequence encoding integrin $\beta_{1C}$, SEQ ID NO:1 or SEQ ID NO:2, or functional fragments thereof, or contacting the cell with a polypeptide having essentially the amino acid sequence of integrin $\beta_{1C}$, SEQ ID NO:1 or SEQ ID NO:2, or functional fragments thereof. The method of the invention can be performed in vitro, in vivo, or ex vivo.

The term "contacting" refers to means of introducing the particular $\beta_{1C}$ reagent to the cell. For example, contacting includes physical/mechanical or chemical means. Physical/mechanical means refers to microinjection or electroporation, for example. Preferably, the $\beta_{1C}$ polynucleotides of the invention are micro-injected into cell nuclei. Chemical means, such as transformation, are described above.

The present invention provides a method for treating a cellular proliferative disorder in a subject, comprising administering to the subject with the therapeutically effective amount of $\beta_{1C}$ integrin reagent which inhibits cellular proliferation. In the method of the invention, the $\beta_{1C}$ integrin reagent comprises a nucleic acid sequence essentially encoding $\beta_{1C}$ integrin or a polypeptide having essentially an amino acid sequence of $\beta_{1C}$ integrin (for sequences, see Argraves, et al, supra; Languino & Ruoslahti, supra). The reagent may be an amino acid sequence consisting essentially of SEQ ID NO:1, or a nucleic acid sequence consisting essentially of a nucleic acid encoding SEQ ID NO:1 or an anti-idiotype antibody which binds to a paratope of an antibody which binds to the amino acid sequence of SEQ ID NO:1. In addition, the reagent may be a peptide consisting essentially of SEQ ID NO:2, a nucleic acid sequence consisting essentially of a nucleic acid encoding SEQ ID NO:2, or an anti-idiotype antibody which binds to a paratope of an antibody which binds to the amino acid sequence of SEQ ID NO:2.

The term "therapeutically effective amount" as used herein refers to the amount of $\beta_{1C}$ reagent of the invention, as described above, administered in sufficient quantity to inhibit cellular proliferation and decrease the symptoms of the cellular proliferative disorder. The dosage ranges for the administration of the polynucleotide, polypeptide, peptide, or anti-idiotype antibody of the invention are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications.

The term "cell-proliferative disorder" denotes malignant as well as non-malignant cell populations which often appear to differ from the surrounding tissue both morphologically and genotypically. For example, the $\beta_{1C}$ reagents described above are useful in treating malignancies of the various organ systems, such as, for example, lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine, and cancer of the esophagus. The $\beta_{1C}$ reagents are also useful in treating non-malignant cell-proliferative diseases such as psoriasis, pemphigus vulgaris, Behcet's syndrome, and lipid histiocytosis. In addition, the method of the invention is useful for inhibiting pathological angiogenesis, for example in disorders of the retina, in arthritis, or in tumors. Essentially, any disorder which is etiologically linked to cellular proliferation would be considered susceptible to treatment with the $\beta_{1C}$ reagents described.

The present invention also provides gene therapy for the treatment of cell proliferative disorders. Such therapy would achieve its therapeutic effect by introduction of the appropriate $\beta_{1C}$ polynucleotide, polypeptide/peptide or anti-idiotype antibody into cells of subjects having the proliferative disorder.

Delivery of sense $\beta_{1C}$ polynucleotide constructs can be achieved using a recombinant expression vector such as a chimeric virus or a colloidal dispersion system.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Most preferably, a non-human primate retroviral vector is employed, such as the gibbon ape leukemia virus (GaLV), thereby providing a broader host range than murine vectors, for example. A number of additional retroviral vectors can incorporate multiple genes. All of these vectors can transfer or incorporate a gene for a selectable marker so that transduced cells can be identified and generated. By inserting a $\beta_{1C}$ polypeptide or peptide nucleotide sequence (including promoter region) of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, methods which allow target specific delivery of the retroviral vector containing the $\beta_{1C}$ polynucleotide.

Since recombinant retroviruses are defective, they require assistance in order to produce infectious vector particles.

This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for $\beta_{1C}$ polynucleotide, polypeptide/peptide, or anti-idiotype antibody is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor. In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting $\beta_{1C}$ anti-id antibody-containing liposomes directly to the malignant tumor. Since the $\beta_{1C}$ gene product may be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an antigenic epitope on the target cells. Liposomes may also be targeted to cells expressing receptors for hormones or other serum factors.

In another aspect, the present invention is directed to polyclonal and monoclonal antibodies which bind to the peptides of the invention. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature,* 256:495, 1975; *Current Protocols in Molecular Biology,* Ausubel, et al., ed., 1989). The term "antibody" as used in this invention includes intact molecules as well as fragments thereof, such as Fab, F(ab')$_2$, and Fv which are capable of binding the epitopic determinant.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the peptides of the invention can be prepared using an intact or full-length $\beta_{1C}$ polypeptide or cytoplasmic fragments containing the peptides of interest as the immunizing antigen. A peptide, such as SEQ ID NO:1, used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal.

If desired, polyclonal antibodies can be further purified, for example, by binding to and elution from a matrix to which the peptide to which the antibodies were raised against is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology,* Wiley Interscience, 1991, incorporated by reference).

Another method for the identification and isolation of an antibody binding domain which exhibits binding with a peptide of the invention is the bacteriophage λ vector system. This vector system has been used to express a combinatorial library of Fab fragments from the mouse antibody repertoire in *Escherichia coli* (Huse, et al., *Science,* 246:1275–1281, 1989) and from the human antibody repertoire (Mullinax, et al., *Proc. Natl. Acad. Sci.,* 87:8095–8099, 1990). As described therein, antibody exhibiting binding for a preselected ligand were identified and isolated from these antibody expression libraries. This methodology can also be applied to hybridoma cell lines expressing monoclonal antibodies with binding for a preselected ligand. Hybridomas which secrete a desired monoclonal antibody can be produced in various ways using techniques well understood by those having ordinary skill in the art and will not be repeated here. For example, where an animal was immunized with peptide/carrier conjugate and hybridomas are later prepared from lymphocytes of the animal, hybridoma producing monoclonal antibody specific for the peptide will bind to peptide, but not carrier, in a standard immunoassay screen. Details of these techniques are described in such references as *Monoclonal Antibodies-Hybridomas: A New Dimension in Biological Analysis,* Edited by Roger H. Kennett, et al., Plenum Press, 1980; and U.S. Pat. No. 4,172,124.

In addition, methods of producing chimeric antibody molecules with various combinations of "humanized" antibodies are known in the art and include combining murine variable regions with human constant regions (Cabily, et al. *Proc. Natl. Acad. Sci.* USA, 81:3273, 1984), or by grafting the murine-antibody complementary determining regions (CDRs) onto the human framework (Riechmann, et al., *Nature* 332:323, 1988).

The antibodies of the invention are immunoreactive and bind with the peptides of the invention. It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. In the present invention, an anti-idiotype antibody, for example, for SEQ ID NO:1, would be the image of amino acid residues which are present in residues 778–825 of the cytoplasmic domain of $\beta_{1C}$ and would inhibit cellular DNA synthesis and proliferation.

The antibodies and peptides of the invention are suited for in vitro use, for example, in immunoassays in which they can be utilized in liquid phase or bound to a solid phase carrier. In addition, the monoclonal antibodies or peptides in these immunoassays can be detectably labeled in various ways. Examples of types of immunoassays which can utilize monoclonal antibodies or peptides of the invention are competitive and non-competitive immunoassays in either a direct or indirect format. Examples of such immunoassays are the radioimmunoassay (RIA) and the sandwich (immunometric) assay. Detection of the antigens using the monoclonal antibodies or antibodies using peptides of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies or peptides of the invention can be bound to many different carriers and used to detect the presence of $\beta_{1C}$ in a cell, for example. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies or peptides, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies or peptides of the invention, or will be able to ascertain such, using routine experimentation. Furthermore, the binding of these labels to the monoclonal antibodies or peptides of the invention can be done using standard techniques common to those of ordinary skill in the art.

For purposes of the invention, $\beta_{1C}$ may be detected by the monoclonal antibodies of the invention when present in biological fluids and tissues. Any sample containing a detectable amount of cells expressing $\beta_{1C}$ can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis. Preferably, the sample is serum.

It is desirable to use the methods described above, for example, in order to detect $\beta_{1C}$ expressing cells. Identification of $\beta_{1C}$ positive cells by antibodies as described herein, may be useful in determining which cells are involved in the cell proliferative disorder or which may be susceptible to treatment by the methods of the invention. The inhibitory ability of peptides described herein, derived from the $\beta_{1C}$ polypeptide, or synthetic equivalents of the peptide, may be used to inhibit undesirable mitotic activity of hematopoietic or platelet cells. Significantly, $\beta_{1C}$ reagents described herein are useful as inhibitors for preventing endothelial cell growth, for example in pathological angiogenesis, or for inhibiting cell proliferation associated with inflammation.

A therapeutic method in accordance with this invention entails the administration of a therapeutic agent of the invention by injection or infusion. The therapeutic agent may be a peptide, polynucleotide, or polypeptide of the invention. In addition, an anti-idiotype antibody which binds to a monoclonal antibody which binds a peptide of the invention may also be used in the therapeutic method of the invention. The amount of therapeutic agent required to inhibit DNA synthesis in a cell depends on such factors as the type and severity of the disorder or infection, the size and weight of the infected subject, and the effectiveness of other concomitantly employed modes of prophylaxis or therapy. The therapeutic method of the invention includes treatment of a subject with a $\beta_{1C}$ reagent following surgical reduction of the tumor burden.

The invention also includes a therapeutic pharmaceutical composition comprising an isolated peptide consisting essentially of the amino sequence of integrin $\beta_{1C}$, SEQ ID NO:1 or SEQ ID NO:2, in combination with a pharmaceutically acceptable carrier and a therapeutic pharmaceutical composition comprising a nucleotide sequence encoding a polypeptide consisting essentially of the amino sequence of $\beta_{62\ 1C}$ SEQ ID NO:1 or SEQ ID NO:2, in combination with a pharmaceutically acceptable carrier. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient is often mixed with excipients which are pharmaceutically acceptable and compatible with the active ingredient. Suitable excipients include water, saline, dextrose, glycerol and ethanol, or combinations thereof. Intravenous vehicles include fluid and nutrient replenishers, electrolyte replenishers, such as those based on Ringer' s dextrose, and the like. Preservatives and other additives may also be present such as, for example, anti-microbials, antioxidants, chelating agents, and inert gases and the like.

A peptide or antibody of the invention can be formulated into the therapeutic composition as neutralized pharmaceutically acceptable salt forms. These include the acid addition salts (formed with the free amino groups of the polypeptide or antibody molecule) and which are formed with inorganic acids such as, for example, hydrochloric or phosphoric acid, or organic acids such as acetic, oxalic, tartaric and the like. Salts also include those formed from inorganic bases such as, for example, sodium, potassium, ammonium, calcium or ferric hydroxides, and organic bases such as isopropylamine, trimethylamine, histidine, procaine and the like.

The invention also envisions the use of antisense or ribozyme sequences for the inhibition of $\beta_{1C}$ gene expression when appropriate. For example, when it is desirable to increase cell proliferation in a cell that expresses $\beta_{1C}$, antisense is introduced into the cell to inhibit $\beta_{1C}$ expression. Therefore, the polynucleotide sequence for $\beta_{1C}$ of the invention, including $\beta_{1C}$ peptides, also includes sequences complementary to the polynucleotide encoding (antisense sequences). Antisense nucleic acids are DNA or RNA molecules that are complementary to at least a portion of a specific mRNA molecule (Weintraub, *Scientific American*, 262:40, 1990). The invention embraces all antisense polynucleotides capable of inhibiting production of polypeptide. In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target-producing cell. The use of antisense methods to inhibit the translation of genes is well known in the art (Marcus-Sakura, *Anal. Biochem.*, 172:289, 1988).

In addition, ribozyme nucleotide sequences for are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The following examples are intended to illustrate but not limit the invention. While they are typical of those that might be used, other procedures known to those skilled in the art may alternatively be used.

EXAMPLES

The present invention shows, for the first time, that an alternatively spliced β1 integrin functions as a potent inhibitor of cell growth. This integrin, named β1 C, was originally identified by Languino and Ruoslahti (supra, 1992) using a PCR strategy. This integrin has a unique 48 amino acid sequence that replaces much of the $\beta_{1C}$ cytoplasmic domain (FIG. 1). The 48 aa alternative cytoplasmic domain has 29% homology to the C-terminal half of the src SH2 domain. $\beta_{1C}$ has been found at low levels in placenta, platelets, hematopoetic cell lines, endothelial cells exposed to rTNF, and in some myelomas (Languino and Ruoslahti, supra, 1992).

The small size of the $\beta_{1C}$ cytoplasmic domain (48 aa) allows the precise structural and functional studies to be undertaken to map the active regions, and that ultimately small molecules could be designed to have similar effects. Inhibitors of cell growth have potential as anti-cancer drugs, either directly by inhibiting tumor cell growth, or indirectly by inhibiting the endothelial cell growth that is required for tumor angiogenesis.

EXAMPLE 1

Preparation of $\beta_{1C}$ Expression Vector

For expression of the $\beta_{1C}$ variant protein of this invention in cells that do not endogenously express the protein, an expression vector containing the cDNA for encoding the $\beta_{1C}$ variant was constructed as described below. The expression vector designated pBJ-1, into which the complete cDNA sequence for encoding the $\beta_{1C}$ variant protein was cloned, was derived from the Srα promoter-based cDNA expression cloning vectors, referred to as pcD-Srα, as described by Takebe, et al., (*Mol. Cell. Biol.*, 8:466–472, 1988), the disclosure of which is hereby incorporated by reference. The pcD-SRα vector utilized a promoter system having the Srα promoter and the SV40 late-gene splicing junction, a vector-primer segment having a KpnI-oligo(dT) priming site, SV40 late-region polyadenylation signal (polyA) and the pUC plasmid-derived vector sequence (the pBR322 replication origin and β-lactamase [AmpR] gene, and also contained nucleotide sequences of the SV40 DNA fragment flanked by the Eco RI and KpnI sites from plasmid pcDVI (Okayama, et al, *Mol. Cell. biol.*, 2:161–170, 1982) and the short DNA fragment from plasmid pL1 (Okayama and Berg, *Mol. Cell. Biol.*, 3:280–289, 1983).

A polylinker comprising the restriction cloning sites XhoI, XbaI, SfiI, NotI, Eco RI, Eco RV, HindIII, ClaI, SalI/XhoI and having the nucleotide sequence 5-CTAGTGGCCTCCGCGGCCGCGAATTCGATATCAAG CTTATCGATCC AGTA-3' (SEQ ID NO:3) was cloned into the XhoI-digested pcD-SRα to form the pBJ-1 expression vector, the schematic of which is shown in FIG. 2. The XhoI digest of pcD-SRα resulted in the deletion of the SV40 late gene splicing junction and the SV40 DNA fragment. The resulting pBJ-1 expression vector was approximately 3.2 kilobases (kb).

To construct a pBJ-1 expression vector from which the $\beta_{1C}$ variant protein was expressed, the pBJ-1 vector was first linearized in the polylinker by digestion with XbaI/NotI. The cDNA encoding the $\beta_{1C}$ (GENBANK Accession No. M84237) was cloned into the pBJ-1 linearized vector with two separate fragments having cohesive ends to allow for directional ligation of the 5' end of wild-type $\beta_1$ cDNA in-frame with the 3' end of wild-type $\beta_1$ cDNA and the $\beta_{1C}$ cDNA sequence. The 5' end of wild-type $\beta_1$ DNA was isolated from a pBLUESCRIPT vector that contained the complete human wild-type $\beta_1$ cDNA sequence. The construction of the wild-type $\beta_1$ cDNA pBLUESCRIPT vector was described by Takada, et al., (*J. Cell. Biol.*, 119:913–921, 1992), the disclosure of which is hereby incorporated by reference. From pBLUESCRIPT, a XbaI/HindIII fragment of approximately 2.3 kb was isolated. The XbaI site was located in the pBLUESCRIPT vector sequence while the HindIII site cut at nucleotide position 2357 of the wild-type $\beta_{1C}$ DNA sequence. The latter sequence has been described by Argraves, et al., (*J. Cell. Biol.*, 105:1 183–1190, 1987), the disclosure of which is hereby incorporated by reference.

The 3' end of the wild-type $\beta_1$ cDNA sequence along with the cDNA sequence encoding the $\beta_{1C}$ variant protein was isolated from the PCR-1000 vector (Invitrogen, San Diego, Calif.) into which a PCR amplified region of $\beta_{1C}$ cDNA had been previously cloned as described by Languino, et al., (*J. Biol. Chem.*, 2677116–7120, 1992), the disclosure of which is hereby incorporated by reference. The amplified fragment having 474 base pairs (bp) began at nucleotide position 2139 in the extracellular domain corresponding to wild-type $\beta_1$ DNA and extended to the 3' end of the $\beta_{1C}$ variant cytoplasmic domain. The PCR-1000 vector containing the $\beta_{1C}$ cDNA was then digested with HindIII/EagI to isolate a DNA fragment of approximately 250 bp. The isolated fragment contained the 3' end wild-type $\beta_1$ DNA beginning at nucleotide position 2358 and extending to 2434 followed by a 116 base pair segment encoding the $\beta_{1C}$ variant cytoplasmic domain starting at nucleotide 2435. The $\beta_{1C}$ variant cytoplasmic 116 bp cDNA and 48 amino acid residue sequence encoded by the cDNA are shown in FIG. 1B. The untranslated wild-type $\beta_1$ DNA followed by PCR-1000 vector sequence ending at EagI polylinker cloning site comprised the rest of the nucleotide sequence in the isolated HindIII/EagI fragment. The complete $\beta_{1C}$ variant cDNA sequence is available under GENBANK™/EMBL Data Bank with Accession Number M84237.

The two isolated fragments described above, the Xba/HindIII fragment containing the 5' end of wild-type $\beta_1$ cDNA and the HindIII/EagI fragment containing the 3' end of wild-type $\beta_1$ and $\beta_{1C}$ variant CDNA encoding the variant cytoplasmic domain, were then directionally ligated by annealing of cohesive ends into the XbaI/NotI-linearized pBJ-1 vector to form the $\beta_{IC}$-pBJ-1 expression vector. NotI and EagI are compatible restriction sites. The $\beta_{1C}$-pBJ-1 vector in *E. coli* strain DH5α was deposited with American Type Culture Collection (ATCC), Manassas, Va., on Oct. 20, 1994.

EXAMPLE 2

Transient Expression of $\beta_{1C}$ IN 10T1\2 cells cDNA coding for human $\beta_{1C}$ (Languino and Ruoslahti, supra) or $\beta_1$ (Argraves, et al., supra) was cloned into the pBJ-1 vector (Takebe, et al., *Mol. Cell Biol.*, 8:466, 1988) and the resulting vector (ATCC 69708 Rockville, Md.) (FIG. 2) was injected directly into the nucleus of quiescent C3H 10T 1\2 murine fibroblasts (ATCC CCL226, Manassas, Va.) by standard microinjection techniques known in the art. This method gives efficient expression of foreign genes even in cells that are not readily transfectable.

Briefly, C3H 10T1\2 cells were injected with either pBJ-1 containing $\beta_{1C}$ or $\beta_1$ cDNA. Wild type human $\beta_1$ cDNA was injected into cells as a control.

Figure 3:
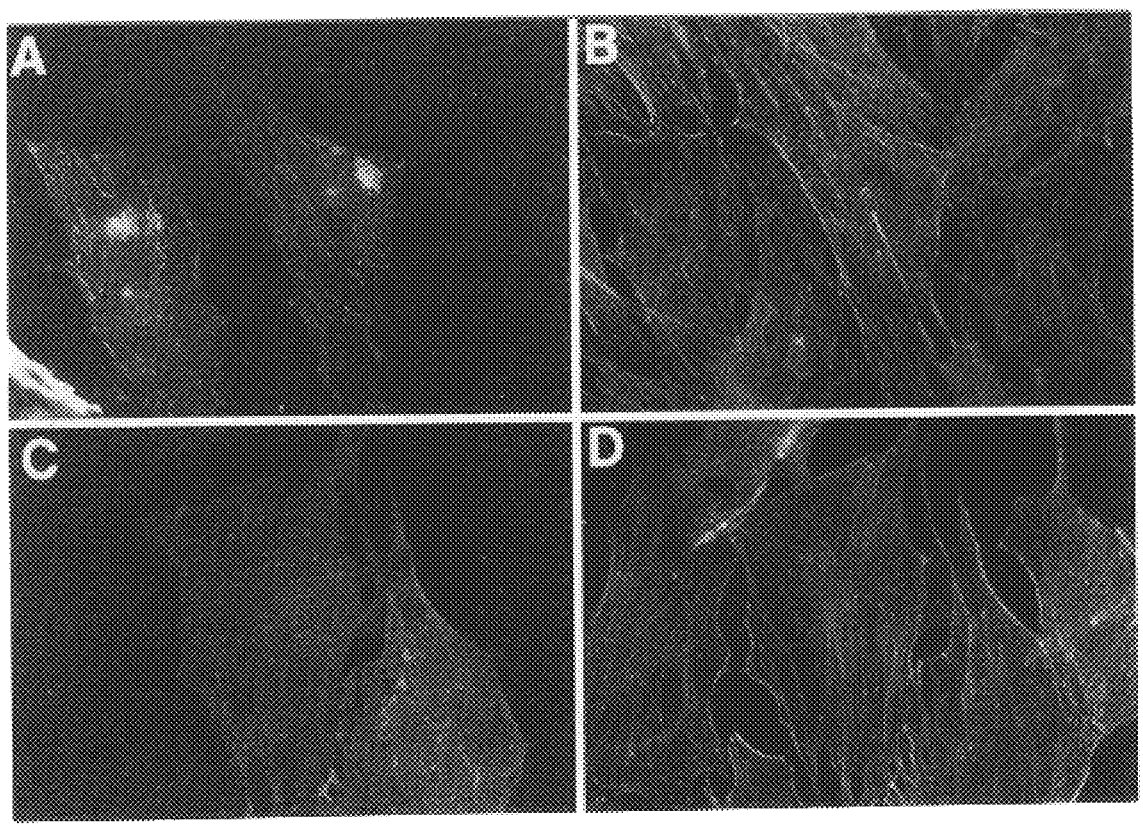
FIGS. 3A–3B show immunostaining for expression and localization of $β_1$ and $β_{1C}$. Cells were injected with cDNAs coding for integrin $β_1$ (FIGS. 3A and 3B) or $β_{1C}$ (FIG. 3C and 3D). After 24 hours, cells were fixed and stained with a rabbit polyclonal antibody against human $β_1$ (FIGS. 3A and 3C) or a mouse monoclonal against vinculin (FIGS. 3B and 3D). The same cell is shown in FIGS. 3A and 3B and in FIGS. 3C and 3D.

FIG. 3 shows the results of cells that were injected with cDNAs coding for integrin $\beta_1$ (Panel A and B) or $\beta_{1C}$ (C and D). After 24 hours, cells were fixed and stained with a rabbit polyclonal antibody produced against purified human $\beta_1$ (A and C) or a mouse monoclonal against vinculin (SIGMA) (B and D). The same cell is shown in A and B and in C and D.

Using standard immunological techniques, both $\beta_{1C}$ and $\beta_1$ were detected on the surfaces of injected cells within 2–3 hours (see, for example, *Current Protocols in Immunology*, Coligan, et al., Wiley Interscience, Inc., 1994). Human $\beta_1$ was recognized by staining the cells with an anti-human polyclonal antibody that does not react with the endogenous mouse integrin. The $\beta_{1C}$ was found diffusely distributed on the cell surface, in contrast to $\beta_1$, which was found localized to focal adhesions (FIG. 3). This pattern was not unexpected, since previous work has shown that the integrin cytoplasmic domain is required for localization to focal adhesions (Hayashi, et al., *J Cell Biol*, 110:175, 1990). At 24–48 hours after injection, $\beta_{1C}$ and $\beta_1$ injected cells showed no obvious change in morphology or appearance, and no change in the structure of the actin cytoskeleton or of focal adhesions when cells were immunostained for vinculin (FIG. 3) or actin. Expression levels of human $\beta_{1C}$ and $\beta_1$ were equivalent in these experiments, as determined by quantitation of fluorescence intensity in surface-stained cells by methods commonly used in the art, and were low compared to endogenous integrins (as determined by surface staining).

EXAMPLE 3

Inhibition of DNA Synthesis by β1C

To assess cell cycle progression, 10% serum and the thymidine analog 5-bromodeoxyuridine (BrdU) were added to injected cultures, and after 24 hr, the cells were fixed and labeled for BrdU incorporation into nuclei by standard methods (see for example, Ausubel, et al., *Current Protocols in Molecular Biology*, John Wiley & Sons, Inc., 1994). Cells were injected with cDNA encoding wild type $\beta_1$, $\beta_1$ with a truncated cytoplasmic domain, or $\beta_{1C}$.

Figure 4:
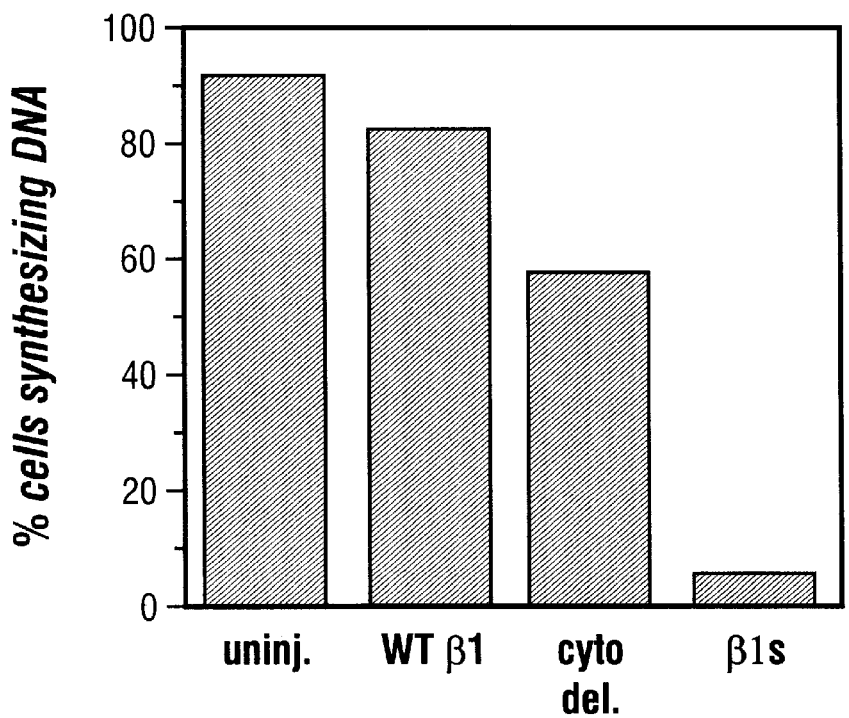
FIG. 4 shows the effect of $β_{1C}$ on DNA synthesis. Cells were injected with cDNA coding for wild type $β_1$, $β_1$ with a truncated cytoplasmic domain, or $β_{1C}$. 10% serum and BdrU were added and after 24 hr, cells were fixed and labeled to detect incorporation of BdrU into nuclei.

Whereas $\beta_1$ had no significant effect, $\beta_{1C}$-positive cells showed a 95% inhibition of DNA synthesis (FIG. 4). As a further control to determine whether expression of any integrin with an altered cytoplasmic domain is growth inhibitory, cells were injected with a cDNA coding for a mutant $\beta_1$ lacking the majority of the cytoplasmic domain. This mutation was previously shown to prevent localization to focal adhesions. Expression of this receptor at levels about 50% higher than those for $\beta_{1C}$ produced only slight inhibition of growth (FIG. 4). This result shows that the $\beta_{1C}$ cytoplasmic domain acts in a dominant fashion to inhibit cell growth. In addition, a truncated $\beta_{1C}$ cDNA having 14aa (SEQ ID NO:2) deleted from the cytoplasmic domain was injected into cells and had no effect on DNA synthesis.

To determine whether binding of $\beta_{1C}$ to extracellular matrix proteins is required for growth inhibition, two methods were used to block ligand binding. First cells were treated with anti-human $\beta_1$ monoclonal antibodies (rabbit polyclonal antibodies produced against purified $\beta_1$) that block ligand binding. Second, $\beta_{1C}$ cDNA containing a point mutation in the extracellular domain that blocks ligand binding was injected into the cells. No reversal of growth inhibition was observed indicating that expression of $\beta_{1C}$ is sufficient to inhibit cell growth.

EXAMPLE 4

Reversal of DNA Synthesis by $\beta_{1C}$ Antibody

To further test whether $\beta_{1C}$ cytoplasmic domain actively inhibits growth, cells injected with $\beta_{1C}$ or $\beta_1$ cDNA were injected 2 hours later with an affinity purified IgG antibody raised against the $\beta_{1C}$ peptide, KKSCLSLPSTWDYRVKIL-FIRVP (SEQ ID NO: 4), as described in Languino and Ruoslahti, supra. DNA synthesis was measured as described above by stimulating cells with 10% serum and addition of BrdU. Cells were analyzed for percent labeled nuclei.

Figure 5:
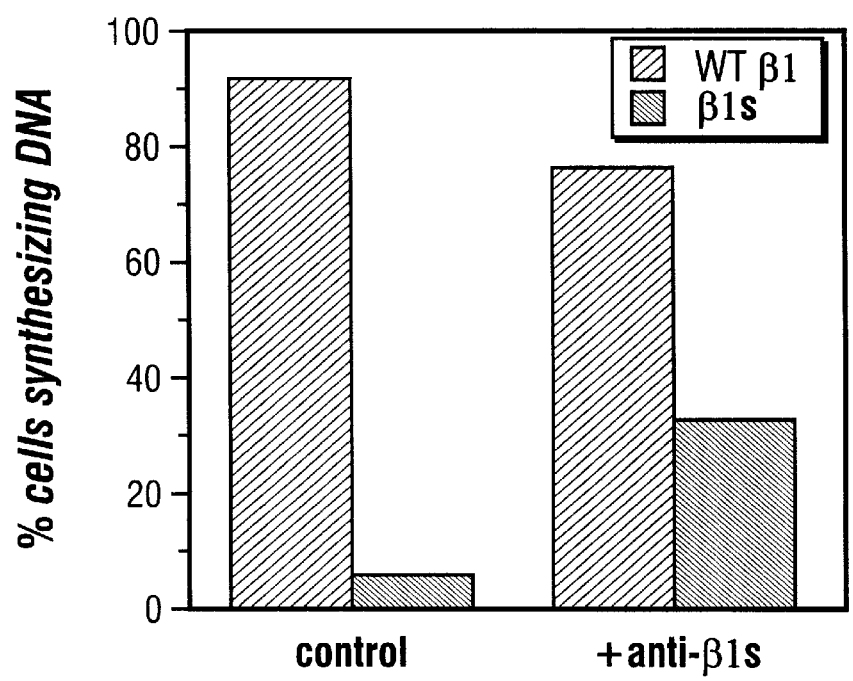
FIG. 5 shows the reversal of cell growth inhibition by antibody. Cells were injected with wild type $β_1$ or $β_{1S}$ cDNA. Two hours later cells were injected with IgG against $β_{1C}$.

Injection of the antibody increased the level of DNA synthesis by about 6–8 fold in $\beta_{1C}$ expressing cells (FIG. 5). The anti-$\beta_{1C}$ IgG restored DNA synthesis to approximately 50% of control levels (relative to cells expressing human $\beta_1$ integrin).

EXAMPLE 5

Chimeric $\beta_{1C}$ Variants

Chimeric receptors are constructed consisting of the transmembrane and extracellular portion of the IL-2 receptor, fused to the $\beta_{1C}$ cytoplasmic domain. A chimeric IL-2 receptor/integrin cytoplasmic domain is already available for the integrin $\beta_1$ subunit (La flamme, et al., *J Cell Biol.*, 117:437, 1992). Second, the $\beta_{1C}$ cytoplasmic domain is expressed as a soluble cytoplasmic protein. These constructs are prepared, and cloned into the BJ-1 expression vector. cDNA's are injected into 10T 1\2 cells and the effects on DNA synthesis are assayed as described above. Analogous constructs with the normal $\beta_1$ ytoplasmic domain are used as controls.

If the IL-2/$\beta_{1C}$ chimera is not growth inhibitory, receptor ligation or clustering is most likely required. Therefore, anti-IL-2 receptor antibodies are used to induce receptor clustering. Antibodies are adsorbed to the coverslips prior to plating cells, or added in solution (with or without second antibody). DNA synthesis is again be assayed. These experiments allow determination of whether the $\beta_{1C}$ cytoplasmic domain is growth inhibitory when soluble in the cytoplasm, when anchored to the inner surface of the plasma membrane, or when clustered in the plasma membrane.

EXAMPLE 6

$\beta_{1C}$ Amino Acid Variants

1. Deletion Variants

To determine if the entire $\beta_{1C}$ cytoplasmic domain is required for growth inhibition, first, receptors with C-terminal deletions are prepared using site-directed mutagenesis by methods known to those of skill in the art. Segments of approximately 8 amino acids are successively deleted, to yield a set of 5 nested deletions. Second, receptors are prepared in which segments from the N-terminus of the alternatively spliced region are deleted. Mutated receptors are then expressed in 10½ cells and DNA synthesis assayed. These experiments enable determination of the critical amino acids $\beta_{1C}$ that are sufficient to inhibit cell growth.

2. Point Mutation Variants

Using the smallest growth inhibitory fragment of $\beta_{1C}$ as a starting point (either a truncated transmembrane receptor or a soluble protein), the effects of point mutations will be analyzed. The "alanine scanning" approach is preferably used in which residues are mutated to alanine, in order to assess the functional role of each residue without disrupting overall structure. Mutants are constructed using standard site-directed mutagenesis techniques known to those of skill in the art; alternatively, if a sufficiently short soluble peptide proved to be growth inhibitory, peptides are prepared synthetically. Peptides or cDNAs are injected and DNA synthesis assayed as above.

EXAMPLE 7

Expression of $\beta_{1C}$ Under Control of an Inducible Promoter

The microinjection method cannot be used for biochemical studies that require large numbers of cells. Because constitutive expression of often prevents cell growth, cells are injected with $\beta_{1C}$ under control of an inducible promoter. Wild-type $\beta_{1C}$, and $\beta_{1C}$ cDNAs are inserted into a vector containing the LACSWITCH System (Stratagene, La Jolla, Calif.). The LACSWITCH expression system gives extremely low levels of basal expression (reported to be ~20 molecules/cell) due to repression by the lac repressor. Upon treatment with the lactose analog IPTG, expression is greatly increased. These cDNAs are transfected into 10½ cells together with a plasmid containing the lactose repressor gene. Cells are selected for G418 resistance, and clones isolated.

Cell lines are treated with IPTG and $\beta_1$ expression analyzed by flow cytometry. Lines that show no expression in the absence of IPTG and good expression in response to IPTG are used for further biochemical studies of $\beta_{1C}$.

DEPOSIT OF MATERIALS

The following cell line has been deposited with the American Type Culture Collection, 10801 University Boulevard, Manassas, Va. 20110-2209, USA (ATCC) on Oct. 20, 1994:

| Cell Line/Vector | ATCC Accession No. |
| --- | --- |
| *E. coli.* DH5 $\alpha\beta_{1C}$-pBJ-1 | 69708 |

The deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC§122 and the Commissioner's rules pursuant thereto (including 37 CFR §1.14 with particular reference to 886 OG 638).

If the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

The invention now being fully described, it will be apparent to one of ordinary skill in the art that many changes and modifications can be made without departing from the spirit or scope of the invention.

We claim:

1. A method of inhibiting cell proliferation in a cell comprising contacting the cell with a polypeptide having the amino acid sequence of integrin $\beta_{1C}$, SEQ ID NO:1 or SEQ ID NO:2.

2. The method of claim 1, wherein the contacting is by physical or chemical means.

3. The method of claim 2, wherein the physical means is microinjection.

4. The method of claim 1, wherein the contacting is in vitro, in vivo, or ex vivo.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 48 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

```
Ser Leu Ser Val Ala Gln Pro Gly Val Gln Trp Cys Asp Ile Ser Ser
1               5                   10                  15

Leu Gln Pro Leu Thr Ser Arg Phe Gln Gln Phe Ser Cys Leu Ser Leu
            20                  25                  30

Pro Ser Thr Trp Asp Tyr Arg Val Lys Ile Leu Phe Ile Arg Val Pro
        35                  40                  45
```

(2) INFORMATION FOR SEQ ID NO:2:

(i) SEQUENCE CHARACTERISTICS:
      (A) LENGTH: 14 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:2:

```
Thr Trp Asp Tyr Arg Val Lys Ile Leu Phe Ile Arg Val Pro
1               5                   10
```

(2) INFORMATION FOR SEQ ID NO:3:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

CTAGTGGCCT CCGCGGCCGC GAATTCGATA TCAAGCTTAT CGATCCAGTA      50

(2) INFORMATION FOR SEQ ID NO:4:

(i) SEQUENCE CHARACTERISTICS:
      (A) LENGTH: 23 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:4:

Lys Lys Ser Cys Leu Ser Leu Pro Ser Thr Trp Asp Tyr Arg Val Lys
1               5                   10                  15

Ile Leu Phe Ile Arg Val Pro
            20

(2) INFORMATION FOR SEQ ID NO:5:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GCCAAATGGG ACACGGGTGA AATCCTATT TATAAGAGTG CCGTAACAAC TGTGGTCAAT      60

CGGAAGTATG AGGGAAAA                                                   78
```

(2) INFORMATION FOR SEQ ID NO:6:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Ala Lys Trp Asp Thr Gly Glu Asn Pro Ile Tyr Lys Ser Ala Val Thr
1               5                   10                  15

Thr Val Val Asn Arg Lys Tyr Glu Gly Lys
            20                  25

(2) INFORMATION FOR SEQ ID NO:7:

(i) SEQUENCE CHARACTERISTICS:
        (A) LENGTH: 194 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GCCAAATGGG ACACGTCTCT CTCTGTCGCC CAGCCTGGAG TGCAGTGGTG TCATATCAGC     60

TTACTGCAAC CTCTGACTTC CAGATTCCAG CAATTCTCCT GCCTCAGCCT CCCGAGTACC    120

TGGGATTACA GGGTGAAAAT CCTATTTATA AGAGTGCCGC AACAACTCTG GTCAATCCGA    180

AGTATGAGGG AAAA                                                     194
```

(2) INFORMATION FOR SEQ ID NO:8:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Ala Lys Trp Asp Thr Ser Leu Ser Val Ala Gln Pro Gly Val Gln Trp
1               5                   10                  15

Cys His Ile Ser Leu Leu Gln Pro Leu Thr Ser Arg Phe Gln Gln Phe
            20                  25                  30

Ser Cys Leu Ser Leu Pro Ser Thr Trp Asp Tyr Arg Val Lys Ile Leu
        35                  40                  45

Phe Ile Arg Val Pro
50
```